United States Patent
Löfroth et al.

(10) Patent No.: US 6,673,365 B1
(45) Date of Patent: Jan. 6, 2004

(54) FORMULATION FOR TREATMENT OF THROMBOEMBOLISM

(75) Inventors: Jan-Erik Löfroth, Mölndal (SE); Lennart Lindfors, Göteborg (SE); Anna-Lena Ungell, Göteborg (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 08/894,615

(22) PCT Filed: May 28, 1997

(86) PCT No.: PCT/SE97/00914

§ 371 (c)(1),
(2), (4) Date: Aug. 22, 1997

(87) PCT Pub. No.: WO97/45138

PCT Pub. Date: Dec. 4, 1997

(30) Foreign Application Priority Data

May 31, 1996 (SE) .............................................. 9602145

(51) Int. Cl.$^7$ .......................... A61K 9/48; A61K 31/505
(52) U.S. Cl. ...................... 424/451; 424/464; 424/474; 514/315; 514/326; 514/772; 514/785; 514/946; 514/256
(58) Field of Search ................................. 514/256, 792, 514/315, 326, 946, 785; 424/451, 464, 474, 19

(56) References Cited

U.S. PATENT DOCUMENTS

| | | | | |
|---|---|---|---|---|
| 4,464,175 A | * | 8/1984 | Altman et al. | 604/99 |
| 4,568,545 A | * | 2/1986 | Mihara et al. | 424/94 |
| 5,795,896 A | * | 8/1998 | Lofroth et al. | 514/256 |

FOREIGN PATENT DOCUMENTS

| WO | WO 9407472 | 4/1994 |
|---|---|---|
| WO | WO 9429336 | 12/1994 |
| WO | WO 9500152 | 1/1995 |
| WO | 9500152 | * 1/1995 |

OTHER PUBLICATIONS

Yeh, et al., Journal of Controlled Release 36, pp. 109–124 (1995).
P. Constantinides, Pharmaceutical Research 12, pp. 1561–1572 (1995).
Constantinides, et al., Pharmaceutical Research 11, pp. 1385–1390 (1994).
Yeh, et al., Pharmaceutical Research 11, pp. 1148–1154 (1994).
Unowsky, et al., Chemotherapy 34, pp. 272–276 (1988).
Van Hoogdalem, et al., J. Pharm. Pharmacol. 40, pp. 329–332 (1987).
Watanabe, et al., J. Pharm. Sci. 77, pp. 847–849 (1988).
Petty, et al., Interscience Conference on Antimicrobial Agents and Chemotherapy, 1986, Abstract No. 1246.
Matsumoto, et al., Chem. Pharm. Bull. 37, pp. 2477–2480 (1989).
Beskid, et al., Chemotherapy 34, pp. 77–84 (1988).
Sekine, et al., J. Pharmacobio–Dyn. 8, pp. 286–295 (1985).
van Hoogdalam, et al., Pharmac. Ther. 44, pp. 407–443 (1989).
S. Muranishi, Critical Reviews™ In Therapeutic Drug Carrier Systems 7, pp. 1–33 (1990).
K. Larsson, Zeitschrift für Physikalische Chemie Neue Folge 56, pp. 199–206 (1967).
Higaki, et al., J. Pharmacobio–Dyn. 9, pp. 532–539 (1986).

* cited by examiner

Primary Examiner—Thurman K. Page
Assistant Examiner—Lakshmi Channavajjala
(74) Attorney, Agent, or Firm—White & Case LLP

(57) ABSTRACT

A new pharmaceutical formulation comprising the thrombin inhibitor HOOC—CH$_2$—(R)-Cgl-Aze-Pab in combination with medium chain glycerides, a process for the preparation of such a pharmaceutical formulation, the use of a such formulation in the treatment of thromboembolism as well as a method of treating a patient in need of such a treatment by using said formulation.

25 Claims, No Drawings

US 6,673,365 B1

FORMULATION FOR TREATMENT OF THROMBOEMBOLISM

FIELD OF THE INVENTION

The present invention relates to a new pharmaceutical formulation comprising the thrombin inhibitor HOOC—CH$_2$—(R)-Cgl-Aze-Pab in combination with one or more absorption enhancing medium chain glyceride lipid agents, a process for the preparation of such a pharmaceutical formulation, the use of the thrombin inhibitor and the absorption enhancing agent for the preparation of a pharmaceutical formulation for the treatment of thromboembolism as well as a method of treating a patient in need of such a treatment by using said formulation.

BACKGROUND

Blood coagulation is the key process involved in both haemostasis (i.e. prevention of blood loss from a damaged vessel) and thrombosis (i.e. the pathological occlusion of a blood vessel by a blood clot). Coagulation is the result of a complex series of enzymatic reactions, where one of the final steps is conversion of the proenzyme prothrombin to the active enzyme thrombin.

Thrombin plays a central role in coagulation. It activates platelets, it converts fibrinogen into fibrin monomers, which polymerize spontaneously into filaments, and it activates factor XIII, which in turn cross-links the polymer to insoluble fibrin. Thrombin further activates factor V and factor VIII in a positive feedback reaction. Inhibitors of thrombin are therefore expected to be effective anticoagulants by inhibition of platelets, fibrin formation and fibrin stabilization. By inhibiting the positive feedback mechanism they are expected to exert inhibition early in the chain of events leading to coagulation and thrombosis.

Peptidic or peptide-like thrombin inhibitors, like many other peptide-like substances, are prone to limited or variable absorption when administered orally. This is due to the influence from different barriers of metabolic and physical character, like enzymatic degradation, tendencies of complex formation with components from the formulation or the biological environment, limitations in transport over the intestinal membranes etc. One object of the pharmaceutical formulation is to facilitate the active agent's overcoming such barriers, and to obtain an enhanced and reproducible absorption of the active agent. Formulation components that have such influence and thus can help the active agent are called absorption enhancers.

PRIOR ART

Concerning the use of absorption enhancers of lipidic origin in pharmaceutical formulations, several reports and reviews in the literature exist. Comprehensive reviews have been presented by E J van Hoogdalem et al., Pharmac Theor vol 44, 407–443 (1989), by S Muranishi, Crit Rev Ther Drug Carrier Syst vol 7, 1–33 (1990), by E S Swenson and W J Curatolo, Adv Drug Deliv Rev vol 8, 39–92 (1992), and in drug Absorption Enhancement (Ed.: A B G de Boer), Harwood Academic Publishers 1994. Specifically, medium chain glycerides have been studied and reported as absorption enhancers in a number of papers, see references above and references therein. The main interest has been to utilize mixtures of mono-, di-, and triglycerides with 6–12 carbon atoms in the chains, i e mono-, di-, and triacylglycerides. More or less well defined samples of glycerides have been used, e g glyceryl mono-octanoate (Tramedico), Capmul MCM (Karlshamns Lipidteknik), Nikkol MGK (Nikko Chemicals), Sunsoft (Taiyo Kagaku), Imwitor (Hüls), Labrasol (Gattefossé), LAS (Gattefossé), and Labrafac Lipo (Gattefossé). Only a few reports deal with effects obtained when the glycerides have been perorally administered (Sekine et al. J Pharmacobio-Dyn 8, 286 (1985); Beskid et al. Chemotherapy 34, 77 (1988)). Several other studies report results when liquid formulations of the glycerides have been administered rectally (Sekine et al. J Pharmacobio-Dyn 7, 856 (1984); ibid 8, 633, 645, and 653 (1985); van Hoogdalem et al. J Pharm Pharmacol 40, 329 (1988), Pharm Res 5, 453 (1988); Unowsky et al. Chemotherapy 34, 272 (1988); Watanabe et al. J Pharm Sci 77, 847 (1988); Matsumoto et al. Chem Pharm Bull 37, 2477 (1989)), or directly as solutions or emulsions by infusion or bolus into different parts of the small intestine (Petty et al. at "Interci Conf on Antimicrobial Agents and Chemotherapy", New Orleans 1986, abstract 1245; Higaki et al. J Pharmacobio-Dyn 9, 532 (1986), Int J Pharm 36, 131 (1987); Yeh et al. Proceed Intern Symp Control Rel Bioact Mater (CRS), 20, 176 (1993); Constantinides et al. CRS 20, 184 (1993); CRS 21, 62 (1994); Marks et al. CRS 22 (1995); Yeh et al. Pharm Res 11, 1148 (1994); Constantinides et al. Pharm Res 11, 1385 (1994), J Controlled Release 34, 109 (1995); Yeh et al. J Controlled Release 36, 109 (1995); Constantinides et al. Pharm Res 12, 1561 (1995)). The glycerides were used either as such, or in mixtures with dispersing agents like lecithins and surfactants to form aggregates like mixed micelles, microemulsions, dispersed lamellar phases etc, or to form self-emulsifying systems. A few patents have also claimed the use of such glycerides in formulations, e g as components in microemulsions (Constantinides WO 94/19003 and references therein), and in selfemulsifying systems with lecithins (Herslöf WO 92/05771 and references therein).

DISCLOSURE OF THE INVENTION

It has been found that the absorption of the thrombin inhibitor HOOC—CH$_2$—(R)-Cgl-Aze-Pab (disclosed in EP 701 568) can be modified beneficially by incorporating medium chain glyceride lipid agents into the pharmaceutical formulations containing said therapeutically active compound.

Therefore, an object of the present invention is to provide novel pharmaceutical formulations comprising the thrombin inhibitor HOOC—CH$_2$—(R)-Cgl-Aze-Pab in combination with one or more medium chain glyceride lipid agents, and a process for the preparation of such pharmaceutical formulations.

The improved formulations of this therapeutically active drug are based on the use of medium chain glycerides to obtain positive synergistic effects which result in an enhanced and/or less variable absorption when the therapeutically active agent is given by different administration routes, such as the oral, the rectal, the buccal, the nasal or the pulmonary route etc.

The formulation may be manufactured with the active peptidic thrombin inhibitor HOOC—CH$_2$—(R)-Cgl-Aze-Pab as commonly used salt or in its base form. The thrombin inhibitor may also be in other stereoisomeric configurations than the one above.

The novel pharmaceutical formulations disclosed in this invention are unique combinations of the thrombin inhibitor HOOC—CH$_2$—(R)-Cgl-Aze-Pab and the medium chain glyceride lipid agents as enhancing agents.

Thus, first, the use of these absorption-enhancing agents in combinations with thrombin inhibitors has not been presented before.

Second, it has been found that glycerides from different sources behave differently, the most efficient enhancing effect being obtained with the pure glyceryl mono-octanoate (1-monocaprylin). Tentatively, the enhancing effects are considered to be due to combinations of several interactions, both between the glycerides and the gastrointestinal membranes, and between the glycerides and the thrombin inhibitor. Thus, the (water-soluble) thrombin inhibitor is soluble in such glycerides without the use of (extra-added) water. Also, the phase diagram displayed by, e.g., the glyceryl monooctanoate in water (Larsson, Zeitschrift Phys Chem Neue Folge 56, 173–198 (1967)) shows that a fluid isotropic phase (L2) is formed at a low water content. These inverted micelles will then provide aggregates with the thrombin inhibitor ready for absorption, the absorption events being enhanced by the presence of the fusogenic lipids. From the phase diagrams of longer medium-chain glycerides, e.g., 1-monocaprin, it can be concluded that the higher temperature needed to obtain a fluid isotropic phase at low water content would make it more difficult for such glycerides to act as enhancers.

Third, it has been found in experiments with different species (rat, dog, human) that a substantial enhancing effect is observed only when the thrombin inhibitor together with the medium-chain glyceride lipid agents are administered directly to the small intestine, that is intraduodenal administration by the use of a duodenal tube, Hg—or tungsten—weighted tube or an endoscopy tube or by enteric coated formulations. On the other hand, direct administration to either the stomach or the colon results in negligible enhancing effects. This is in sharp contrast to most other reports on enhancing effects from medium-chain glycerides.

Fourth, the formulations disclosed here are based on the use of medium-chain glycerides, and mixtures thereof, without the requirements of dispersing the lipids with other agents such as emulsifiers for producing microemulsions, lecithins to provide self-emulsifying systems, or any other similar agents. Further, it is worth emphasizing that no water is needed in the formulation according to the invention.

Medium chain glycerides according to the present invention are defined as compounds of the formula

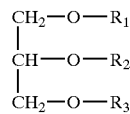

wherein $R_1$, $R_2$ and $R_3$ are the same or different and each represents a hydrogen atom or acyl group having 6–12 carbon atoms provided that at least one of $R_1$, $R_2$ and $R_3$ is an acyl group.

The dosage form used may be a solid, semisolid or liquid preparation prepared by per se known techniques. Usually the active substance will constitute between 0.1 and 99% by weight of the preparation.

Suitable daily doses of the therapeutically active drug in therapeutic treatment of humans are about 0.001–100 mg/kg body weight at peroral administration.

The enhancing agent, or combinations of enhancing agents, will constitute between 0.1 and 99% by weight of the preparation. The formulations thus obtained will increase the absorption and/or minimize the variability of the absorption of the therapeutically active drug by different mechanisms.

The pharmaceutical formulations of the present invention comprising the modified dipeptide HOOC—CH$_2$—(R)-Cgl-Aze-Pab and the absorption enhancing agent are intended for prophylaxis and treatment in arterial as well as venous thromboembolism.

DETAILED DESCRIPTION OF THE INVENTION

The following description is illustrative of aspects of the invention.

EXPERIMENTAL PART

Preparation of the Formulations

Formulation A: HOOC—CH$_2$—(R)-Cgl-Aze-Pab (base) 0.43 mg/ml

Akoline (Capmul MCM)

Phosphate buffer 0.1 M, pH 8.0

1 ml of formulation contains 0.9 g of akoline+0.1 g of buffer+0.43 g of drug. Akoline was heated to 30° C. and was mixed with the buffer containing the thrombin inhibitor HOOC—CH$_2$—(R)-Cgl-Aze-Pab in the proportion of akoline:water 90:10.

Formulation B: HOOC—CH$_2$—(R)-Cgl-Aze-Pab (base) 0.43 mg/ml

Akoline (Capmul MCM)

1 ml of formulation contains 1 g of akoline+0.43 g of drug. Akoline was heated to 30° C. and was mixed with the thrombin inhibitor HOOC—CH$_2$—(R)-Cgl-Aze-Pab (base).

Formulation C: HOOC—CH$_2$—(R)-Cgl-Aze-Pab (base) 0.43 mg/ml

Monoglyceride C8:0

Monoglyceride C10:0

Phosphate buffer 0.1 M, pH 8.0

1 ml of formulation contains 0.7 g of C8:0+0.26 g of C10:0+0.04 g of buffer+0.43 g of drug. Monoglyceride C8:0 was heated to 35° C. and the monoglyceride C10:0 was heated to 70° C. The mono-C10:0 was added to the mono-C8:0 in the proportions 26:70 respectively and the buffer solution containing the thrombin inhibitor HOOC—CH$_2$—(R)-Cgl-Aze-Pab was added into the mixture to a total of 4%. The mixture was then shaken and kept warm (30° C.) before administration.

Formulation D: HOOC—CH$_2$—(R)-Cgl-Aze-Pab (base) 0.43 mg/ml

Monoglyceride C8:0

Phosphate buffer 0.1 M, pH 8.0

1 ml of formulation contains 0.95 g of C8:0+0.05 g of buffer+0.43 g of drug. Monoglyceride C8:0 was heated to 30° C. and the thrombin inhibitor HOOC—CH$_2$—(R)-Cgl-Aze-Pab in phosphate buffer was added to the mixture to a total amount of 5%. The mixture was then shaken before administration.

The formulations, A to D, respectively, were tested in vivo in the rat model using intraduodenally catheterized, nonanesthetized animals. Formulations were given as a bolus. Blood samples were withdrawn at certain time points for up to 4 hours after administration of the different formulations. The concentrations of HOOC—CH$_2$—(R)-Cgl-Aze-Pab were analyzed in the plasma and the bioavailabilities calculated from the Area under the curve (AUC) using standard pharmacokinetic methods (Rowland and Tozer, Clinical Pharmacokinetics, concepts and applications, 1980).

The results from the tested formulations A to D in vivo in the rat are presented in Table 1 as formulations 2–5. The bioavailability increased tenfold to twentyfold when the different formulations mentioned in the invention were used, as compared to controls where only phosphate buffer of pH 8 was used (1). Formulation B was also tested in human healthy subjects using enteric coated capsules for administration directly to the duodenum. The results from the human study also indicate a tenfold increased absorption as compared to a control tablet or solution of the thrombin inhibitor base only.

All formulations tested containing the mono and/or di glycerides C8 and C10 increased the bioavailability of the thrombin inhibitor HOOC—$CH_2$—(R)-Cgl-Aze-Pab surprisingly well from the upper GI tract.

Abbreviations

Aze=(S)-Azetidine-2-carboxylic acid
Cgl=(S)-Cyclohexyl glycine
Pab=1-Amidino-4-aminomethyl benzene

TABLE 1

Bioavailability of HOOC—$CH_2$-(R)-Cgl-Aze-Pab in vivo in the rat after administration intraduodenally with formulations containing monoglycerides or mono- and diglyceride mixtures described in the invention. Numbers represent the mean values ± SD, where N indicates the number of animals used.

| | Formulation | Bioavailability (%) mean | SD | N |
|---|---|---|---|---|
| 1. | Phosphate buffer 0.1M, pH 8.0 | 3.0 | 2.5 | 4 |
| 2. | Capmul:water 90:10 | 37.2 | 9.2 | 4 |
| 3. | Capmul 100% | 55.5 | 14.6 | 4 |
| 4. | Mono-C8/C10: water 96:4 | 47.8 | 8.6 | 3 |
| 5. | Mono C8:water 95:5 | 73 | 5.1 | 3 |

What is claimed is:

1. A pharmaceutical formulation comprising the therapeutically active compound HOOC—$CH_2$—(R)-Cgl-Aze-Pab or a physiologically acceptable salt thereof and one or more absorption enhancing agents selected from the group of a mono-, di- or triglyceride comprising at least one acyl group of chain length of 6 to 12 carbon atoms.

2. A pharmaceutical formulation according to claim 1 wherein the acyl group contains 8 to 10 carbon atoms.

3. A pharmaceutical formulation according to claim 1 wherein the absorption enhancing agent is selected from mixtures of mono-, di- or triglycerides with acyl groups containing 8 carbon atoms.

4. A pharmaceutical formulation according to claim 1 wherein the absorption enhancing agents is selected from mixtures of mono- or diglycerides having acyl groups of 6 to 12 carbon atoms.

5. A pharmaceutical formulation according to claim 1 wherein the absorption enhancing agent is selected from mixtures of mono- or diglycerides having acyl groups of 8 to 10 carbon atoms.

6. A pharmaceutical formulation according to claim 1 wherein the absorption enhancing agent is selected from mixtures of mono- or diglycerides having acyl groups of 8 carbon atoms.

7. A pharmaceutical formulation according to claim 1 wherein the absorption enhancing agent is selected from mixtures of monoglycerides having acyl groups of 6 to 12 carbon atoms.

8. A pharmaceutical formulation according to claim 1 wherein the absorption enhancing agent is selected from mixtures of monoglycerides having acyl groups of 8 to 10 carbon atoms.

9. A pharmaceutical formulation according to claim 1 wherein the absorption enhancing agent is a monoglyceride having a 6-carbon acyl group.

10. A pharmaceutical formulation according to claim 1 wherein the absorption enhancing agent is a monoglyceride having an 8-carbon acyl group.

11. A pharmaceutical formulation according to claim 1 wherein the absorption enhancing agent is a monoglyceride having a 10-carbon acyl group.

12. A pharmaceutical formulation according to claim 1 wherein the absorption enhancing agent is a monoglyceride having a 12-carbon acyl group.

13. A pharmaceutical formulation according to claim 1 wherein the absorption enhancing agent is selected from mixtures of diglycerides having acyl groups of 6 to 12 carbon atoms.

14. A pharmaceutical formulation according to claim 1 wherein the absorption enhancing agent is selected from mixtures of diglycerides having acyl groups of 8 to 10 carbon atoms.

15. A pharmaceutical formulation according to claim 1 wherein the absorption enhancing agent is a diglyceride having acyl groups of 6 carbon atoms.

16. A pharmaceutical formulation according to claim 1 wherein the absorption enhancing agent is a diglyceride having acyl groups of 8 carbon atoms.

17. A pharmaceutical formulation according to claim 1 wherein the absorption enhancing agent is a diglyceride having acyl groups of 10 carbon atoms.

18. A pharmaceutical formulation according to claim 1 wherein the absorption enhancing agent is a diglyceride having acyl groups of 12 carbon atoms.

19. A mixture comprising the therapeutically active compound HOOC—$CH_2$—(R)-Cgl-Aze-Pab or a physiologically acceptable salt thereof and one or more absorption enhancing agents selected from the group of a mono-, di- or triglyceride comprising at least one acyl group of chain length of 6 to 12 carbon atoms.

20. A method of treating a patient in need of antithrombolic treatment comprising administering to said patient a pharmaceutical formulation as defined in any one of claims 1 to 19 directly to the small intestine.

21. A method according to claim 20 wherein the administration is by use of a duodenal tube, mercury or tungsten weighted tube or an endoscopy tube.

22. A pharmaceutical formulation according to claim 1 wherein the absorption enhancing agent forms micelles which provide aggregates with the thrombin inhibitor.

23. A method according to claim 20 wherein the formulation is enteric coated.

24. A substantially nonaqueous pharmaceutical formulation according to claim 1.

25. A pharmaceutical formulation according to claim 1 which contains no water.

* * * * *